(12) United States Patent  (10) Patent No.: US 12,131,172 B2
Azizian et al.  (45) Date of Patent: Oct. 29, 2024

(54) TECHNIQUES FOR VIRTUALLY RECREATING DEVICES

(71) Applicant: INTUITIVE SURGICAL OPERATIONS, INC., Sunnyvale, CA (US)

(72) Inventors: Mahdi Azizian, Santa Clara, CA (US); Jonathan Sorger, Belmont, CA (US); Simon P. Dimaio, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 226 days.

(21) Appl. No.: 17/544,654

(22) Filed: Dec. 7, 2021

(65) Prior Publication Data

US 2022/0091867 A1  Mar. 24, 2022

Related U.S. Application Data

(63) Continuation of application No. 16/142,937, filed on Sep. 26, 2018, now Pat. No. 11,221,863, which is a (Continued)

(51) Int. Cl.
*G06F 11/34* (2006.01)
*G06F 9/455* (2018.01)
(Continued)

(52) U.S. Cl.
CPC .......... *G06F 9/455* (2013.01); *G06F 11/3476* (2013.01); *G09B 23/28* (2013.01);
(Continued)

(58) Field of Classification Search
CPC ..... G06F 9/455; G06F 11/3476; G09B 23/28; G16H 40/63; G16H 40/67; G16H 50/50; G16Z 99/00; H04L 67/01
See application file for complete search history.

(56) References Cited

U.S. PATENT DOCUMENTS 6,928,490 B1   8/2005  Bucholz et al.
7,613,597 B2  11/2009  Vertes
(Continued)

FOREIGN PATENT DOCUMENTS

CN  101055538 A  10/2007
CN  101107598 A   1/2008
(Continued)

OTHER PUBLICATIONS

Geels, D., et al. "Replay Debugging for Distributed Applications" USENIX Annual Technical Conf., pp. 289-300 (2006) (Year: 2006).*
(Continued)

*Primary Examiner* — Jay Hann
(74) *Attorney, Agent, or Firm* — Artegis Law Group, LLP

(57) ABSTRACT

Techniques for virtually recreating devices include a replay service configured to access a log associated with a first device, extract a first log entry from the log, recreate a first recreated service request for the one or more shared services based on information associated with the first log entry, and send the first recreated service request to a shared service to recreate an event associated with the first log entry; one or more shared services configured to receive and respond to a second service request from a second device coupled to the logging and replay device; and a recreation engine configured to receive the first recreated service request, a response to the first recreated service request, the second service request, and a response to the second service request and create a virtual recreation of the first device.

20 Claims, 5 Drawing Sheets

Related U.S. Application Data continuation of application No. 14/912,079, filed as application No. PCT/US2014/051055 on Aug. 14, 2014, now Pat. No. 10,127,060.

(60) Provisional application No. 61/866,957, filed on Aug. 16, 2013.

(51) Int. Cl.
*G09B 23/28* (2006.01)
*G16H 40/63* (2018.01)
*G16H 40/67* (2018.01)
*G16H 50/50* (2018.01)
*G16Z 99/00* (2019.01)
*H04L 67/01* (2022.01)

(52) U.S. Cl.
CPC ............ *G16H 40/63* (2018.01); *G16H 40/67* (2018.01); *G16H 50/50* (2018.01); *G16Z 99/00* (2019.02); *H04L 67/01* (2022.05)

(56) References Cited

U.S. PATENT DOCUMENTS

| | | | | |
|---|---|---|---|---|
| 7,930,684 | B2* | 4/2011 | Roeck | G06F 11/2046 717/130 |
| 8,402,318 | B2* | 3/2013 | Nieh | G06F 11/3419 717/124 |
| 8,442,941 | B2* | 5/2013 | Yao | G06F 11/3461 707/610 |
| 8,469,713 | B2 | 6/2013 | Kron et al. | |
| 8,478,800 | B1 | 7/2013 | Johnson et al. | |
| 8,869,174 | B2 | 10/2014 | Wong | |
| 8,961,188 | B1 | 2/2015 | Singh et al. | |
| 9,104,739 | B2* | 8/2015 | Liang | G06F 11/3495 |
| 9,384,112 | B2 | 7/2016 | Petersen et al. | |
| 9,396,669 | B2 | 7/2016 | Karkanias et al. | |
| 9,585,562 | B2 | 3/2017 | Sobie et al. | |
| 9,846,721 | B2 | 12/2017 | Gatto et al. | |
| 10,078,669 | B2 | 9/2018 | Borowiec et al. | |
| 10,127,060 | B2 | 11/2018 | Azizian et al. | |
| 2003/0172198 | A1 | 9/2003 | Tiwary et al. | |
| 2006/0004862 | A1 | 1/2006 | Fisher et al. | |
| 2006/0270913 | A1* | 11/2006 | Todd | A61B 90/00 600/300 |
| 2007/0203976 | A1 | 8/2007 | Bein et al. | |
| 2008/0225718 | A1 | 9/2008 | Raja et al. | |
| 2009/0081951 | A1 | 3/2009 | Erdmann et al. | |
| 2009/0125581 | A1 | 5/2009 | Schneider | |
| 2009/0199047 | A1 | 8/2009 | Vaitheeswaran et al. | |
| 2009/0276515 | A1 | 11/2009 | Thomas et al. | |
| 2011/0238379 | A1* | 9/2011 | Misra | G16H 40/67 702/187 |
| 2013/0047103 | A1 | 2/2013 | Avisar | |
| 2019/0026133 | A1 | 1/2019 | Azizian et al. | |

FOREIGN PATENT DOCUMENTS

| | | |
|---|---|---|
| CN | 103064905 A | 4/2013 |
| JP | 2005025361 A | 1/2005 |
| JP | 2006102108 A | 4/2006 |
| JP | 2008272301 A | 11/2008 |
| JP | 2011039877 A | 2/2011 |
| JP | 2011087962 A | 5/2011 |
| KR | 20130030678 A | 3/2013 |

OTHER PUBLICATIONS

Narayanasamy, S., et al. "BugNet: Recording Application Level Execution for Deterministic Replay Debugging" IEEE Micro, vol. 26, issue 1, pp. 100-109 (2006) available from <https://ieeexplore.ieee.org/abstract/document/1603502> (Year: 2006).*

DiMaio, S., Hanuschik, M. & Kreaden, U. "Ch 9: The da Vinci Surgical System" Surgical Robotics: Systems Applications & Visions ( 2011) (first online Jan. 2010) (Year: 2010).*

International Search Report and Written Opinion for Application No. PCT/US14/51055, mailed on Nov. 26, 2014, 10 pages (ISRG05700/PCT).

Magnusson P.S., et al., "Simics: A Full System Simulation Platform," IEEE Computer, Feb. 2002, vol. 35 (2), pp. 50-58.

Moon, B., et al. "Scalable Algorithms for Large Temporal Aggregation" IEEE 16th Int'l Conf. on Data Engineering (2002) available from https://ieeexplore.ieee.org/abstract/document/839401 (Year: 2002).

Sah A., "A New Architecture for Managing Enterprise Log Data" USENIX Lisa 2002—16th Systems Administration Conf. (2002) available at [URL: https://www.usenix.org/legacy/events/lisa02/tech/full_papers/sah/sah_html/] (Year:2002), 12 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

TECHNIQUES FOR VIRTUALLY RECREATING DEVICES

RELATED APPLICATIONS

This application is a continuation of U.S. patent application Ser. No. 16/142,937 (filed on Sep. 26, 2018), which is a continuation of U.S. patent application Ser. No. 14/912,079 (filed on Feb. 12, 2016), which is a U.S. National Stage patent application of International Patent Application No. PCT/US2014/051055 (filed on Aug. 14, 2014), the benefit of which is claimed, and claims priority to U.S. Provisional Patent Application No. 61/866,957 (filed on Aug. 16, 2013), the disclosures of each of which are hereby incorporated by reference in their entirety.

TECHNICAL FIELD

The present disclosure relates generally to interoperability among heterogeneous devices and more particularly to logging and replay among heterogeneous devices.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and basic metal scalpels are being replaced by computer-assisted medical devices.

These electronic devices provide both advantages and challenges to the personnel operating them. Each of these electronic devices may be capable of providing large volumes of both accurate and precise data regarding patient conditions, the state of the electronic devices, and so forth. However, because each of these different electronic devices monitor and/or operate using different data and perform different tasks, they form a heterogeneous collection of devices. And despite the presence of programmable processors and microprocessors in many of these heterogeneous devices, the ability of these heterogeneous devices to share data and information and to coordinate their respective operations is often significantly underutilized.

In many cases, there is little to no exchange of data and information between the heterogeneous devices. One reason for this is that many of the heterogeneous devices in an operating room or interventional suite are provided by different vendors. Other reasons include differences between various models of devices and even the different tasks each of the medical devices is designed to perform. Consequently, many operating rooms and interventional suites are filled with heterogeneous medical devices that are not aware of each other and do not exchange data and information between themselves, much less exhibit any kind of significant interoperability. Instead, medical personnel are often expected to monitor and operate each of the devices independently or the devices must be used in such a way that they do not interfere with each other. For example, a computer-assisted surgical device may only be permitted in areas of the operating room where it won't interfere or collide with an imaging system also present in the operating room. Such a restriction may limit the functionality of both the computer-assisted surgical device and the imaging system.

One approach to supporting the exchange of data and information between heterogeneous devices and other forms of interoperability involves joint development efforts between the vendors or design teams of a single vendor. This may include the development of custom hardware and/or software to permit two different heterogeneous devices to exchange data and information and to interoperate. These types of development efforts are often very time consuming and expensive and often require extensive testing and maintenance. They further provide only a limited solution to the larger interoperability problem as they only address issues between the two specific heterogeneous devices. The development work may not extend to other devices, even in the same product line, and likely will not extend to other types of devices and devices from other vendors. These development efforts may further introduce complications associated with the exchange of intellectual property, such as trade secrets, and difficulty identifying the owner of the final product.

Accordingly, it would be desirable to provide improved methods and systems for supporting interoperability between heterogeneous devices. It would further be desirable to provide improved methods and systems for supporting logging and replay among the heterogeneous devices.

SUMMARY

Consistent with some embodiments, a logging and replay device includes one or more shared services including a replay service, a processor for executing the one or more shared services, and a shared interface for providing access to the one or more shared services. The replay service is configured to select one or more logs for playback, emulate one or more playback devices, each of the playback devices being associated with a respective one of the logs, extract one or more log entries from each of the logs, recreate one or more recreated service requests for the one or more shared services based on information associated with each of the log entries, and initiate the recreated service requests.

Consistent with some embodiments, a method of logging and replay includes selecting one or more logs for playback, emulating one or more playback devices, each of the playback devices being associated with a respective one of the logs, extracting one or more log entries from each of the logs, recreating one or more recreated service requests for one or more shared services based on information associated with each of the log entries, and initiating the recreated service requests by sending them to a corresponding one of the one or more shared services using a shared interface.

Consistent with some embodiments, a logging and replay system includes a logging and replay server, one or more heterogeneous devices coupled to the logging and replay server, and one or more logs. The logging and replay server includes one or more shared services including a replay service, a processor for executing the one or more shared services, and a shared interface for providing access to the one or more shared services. The replay service is configured to emulate one or more playback devices, each of the playback devices being associated with a respective one of the logs, extract one or more log entries from each of the logs, recreate one or more recreated service requests for the one or more shared services based on information associated with each of the log entries, and initiate the recreated service requests. The one or more shared services are configured to receive and respond to one or more live service requests from the one or more heterogeneous devices.

In the figures, elements having the same designations have the same or similar functions.

DETAILED DESCRIPTION

In the following description, specific details are set forth describing some embodiments consistent with the present disclosure. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
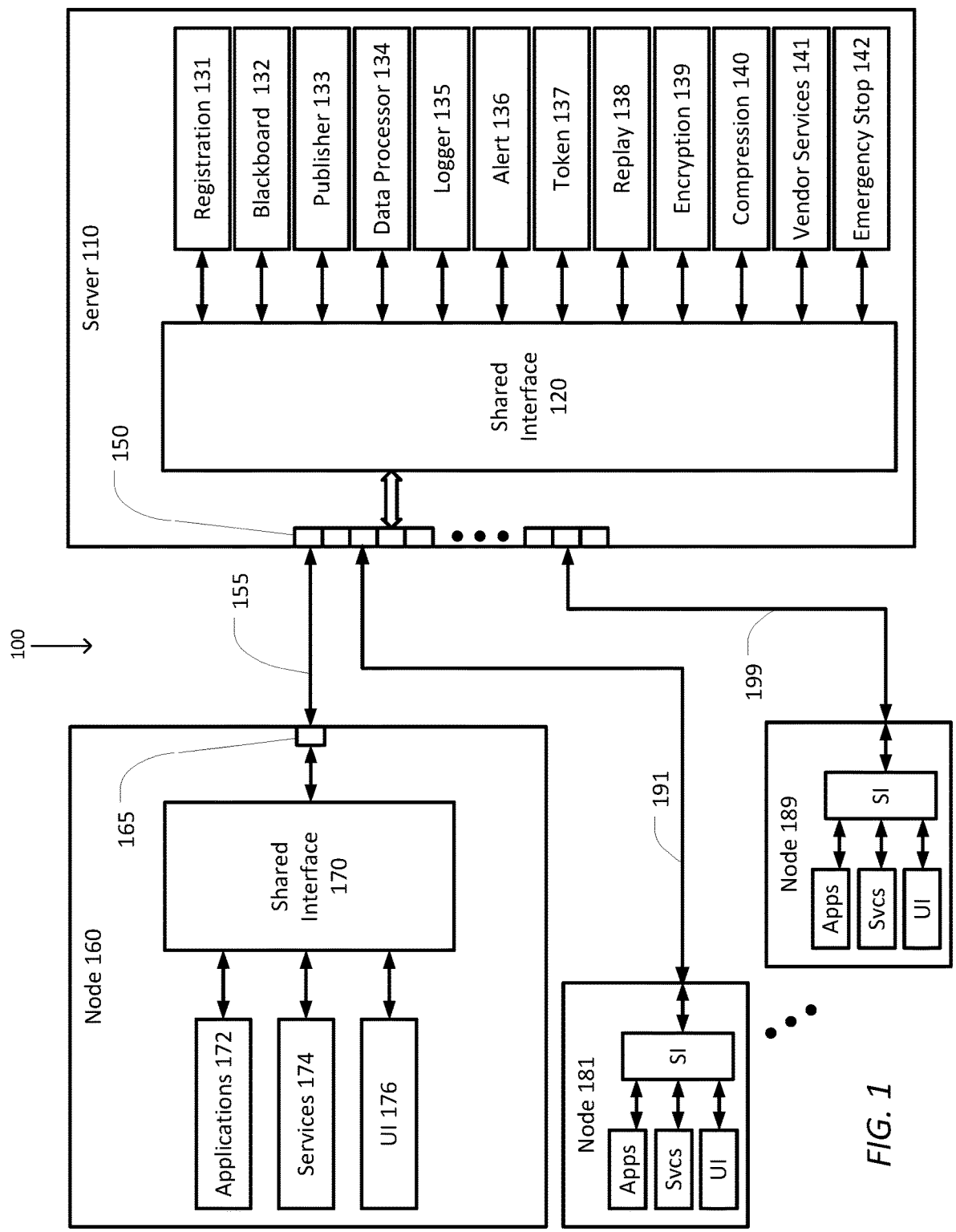
FIG. 1 is a simplified diagram of an interoperability system according to some embodiments.

FIG. 1 is a simplified diagram of an interoperability system 100 according to some embodiments. As shown in FIG. 1, interoperability system 100 includes a server 110 for acting as an interoperability point for interoperability system 100. Server 110 may be a workstation or any other kind of computing device, including one or more clustered computing devices, and as such it may be a stand-alone component or embedded in one or more medical devices. Although not shown in FIG. 1, server 110 may include one or more processors and memory. The memory may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Server 110 includes a shared interface 120 designed to support and standardize communication and interoperability between heterogeneous medical devices that are coupled to shared interface 120. The heterogeneous devices may include one or more devices that perform different tasks and/or may be provided by different vendors. In some examples, the heterogeneous devices may include two or more devices of the same type, model, and version. Shared interface 120 provides a known hardware and software interface that each of the heterogeneous devices may use. Shared interface 120 may further receive requests from the heterogeneous devices. In some examples, the requests may be generated by the heterogeneous devices and received by shared interface 120 using mechanisms such as application programming interface (API) calls, remote procedure calls, web services calls, message passing, and/or the like. Shared interface 120 may also transmit data and/or other information back to the heterogeneous devices to further support interoperability. In some examples, shared interface 120 may be implemented using a layered software stack and/or a combined hardware and software stack.

To support interoperability between the heterogeneous devices, server 110 may further include support for a flexible collection of service modules or services. In some examples, the services may include one or more of the following services, a registration service 131, a blackboard service 132, a publisher service 133, a data processing service 134, a logging service 135, an alert service 136, a token service 137, a replay service 138, an encryption service 139, a compression service 140, vendor services 141, an emergency stop service 142, and/or the like. Although only services 131-142 are shown in FIG. 1, this list of services 131-142 is illustrative only and not limiting. Any one or more of the services 131-142 may be omitted and/or other services not described may be added. Each of the services may add additional functionality to support interoperability and the services may be mixed and matched depending on the type and level of interoperability desired between the heterogeneous devices. In some examples, server 110 may also provide additional services not shown in FIG. 1. In some examples, services may be added and/or removed from server 110 by using one or more plug-ins supported by shared interface 120.

Registration service 131 includes support for registering and/or authenticating users and/or heterogeneous devices that use the other services, such as services 132-142, provided by server 110. In some examples, registration service 131 may provide a login mechanism using a username and password for limiting access to server 110 to only authorized users and/or heterogeneous devices. In some examples, upon successful registration, an authenticated user and/or heterogeneous device may be provided with one or more keys and/or session identifiers. The one or more keys and/or session identifiers may be used to identify the user and/or heterogeneous device with the other services 132-142 provided by server 110. The one or more keys and/or session identifiers may also be used to encrypt and/or decrypt data and other information exchanged between the users and/or the heterogeneous devices and server 110 and/or data stored in server 110.

In some examples, registration service 131 may further maintain one or more access control lists used by shared interface 120 and/or services 132-142 to limit access to services 132-142. In some examples, the process of registration with registration service 131 may further include identifying a type of heterogeneous device connecting to server 110. The type of heterogeneous device may include information such as a vendor and model number of the heterogeneous device, a firmware version number, a classification for the heterogeneous device, and/or the like. The classification may include categories such as computer-assisted medical device, imaging device, cardiac monitor, and/or the like. In some examples, registration service 131 may provide registration at the application level rather than the device level so that different applications supported by the same heterogeneous device may have different levels of access to server 110 and services 132-142. In some examples, registration service 131 may update one or more data structures necessary to manage its functionality.

Blackboard service 132 provides a memory area that may be shared among the heterogeneous devices. Each of the heterogeneous devices registered with the server 110 and the shared interface 120 may use blackboard service 132 to record data and information that may then be shared with other heterogeneous devices. For example, a computer-assisted surgical device and/or an imaging system may supply information associated with no-fly zones that represent areas and/or volumes in which entry is not permitted, component positioning, and/or motion path planning to blackboard service 132 so that other movable devices may coordinate their movements accordingly.

In some embodiments, blackboard service 132 may store data in the shared memory area using a key-value pair approach. When a heterogeneous device provides data to blackboard service 132, the data may be associated with a unique key that may be used to retrieve the data later. The key may be supplied by the heterogeneous device supplying the data, or it may be generated by blackboard service 132. In some examples, data exchanged between blackboard service 132 and the homogeneous devices may be exchanged using one or more protocols including hypertext transport protocol (HTTP), user datagram protocol (UDP), extensible markup language (XML), health level 7 (HL7), digital imaging and communication in medicine (DICOM), Controller Area Network (CAN), Fieldbus (IEC61158), Process Field Bus (Profibus), and/or the like. In some examples, blackboard service 132 may further encrypt and/or compress one or more data items in the shared memory for security purposes. In some examples, blackboard service 132 may rely on encryption service 139 and/or compression service 140 to perform encryption/decryption and/or compression/decompression. In some examples, blackboard service 132 may use the one or more access control lists maintained by registration service 131 to limit access to some of the data in the shared memory to a subset of applications and/or other heterogeneous devices. In some examples, blackboard service 132 may also provide support for locking of data in the shared memory that may temporarily make portions of the data in the shared memory unavailable to other heterogeneous devices.

Publisher service 133 provides a publish-subscribe mechanism for proactively sharing data and information between the heterogeneous devices. Using publisher service 133, heterogeneous devices may subscribe to notifications and/or callbacks associated with other data and information published to publisher server 133 by other heterogeneous devices. For example, a heterogeneous device may request to be notified or receive a callback whenever an update is made to data stored in the shared memory of blackboard service 132, such as when an imaging device makes a new image available. In some examples, publisher service 133 may support conditional checks on the updated data before sending out a notification. In some examples, the conditional checks may include one or more Boolean tests based on range checks, locking status, and/or other tests based on the values or status of data. As with blackboard service 132, publisher service 133 may additionally support encryption, compression, and/or access control lists, or it may rely on other services such as encryption service 139 and/or compression service 140 to provide this functionality.

Data processing service 134 provides scripting and post-processing of data supplied to shared interface 120. In some examples, data processing service 134 may perform data fusion, aggregation, and/or statistical analysis of data and information stored using blackboard service 132. The data fusion and statistical analysis may, for example, include computing a running and/or weighted average and/or estimate noise parameters of numerical values stored using blackboard service 132. In some examples, data processing service 134 may support a scripting language allowing other heterogeneous devices to supply simple and/or complex scripts to be executed on stored data that may additionally be used in conjunction with the notifications and callbacks of publisher service 133. In some examples, data processing service 134 may receive custom processing scripts from the heterogeneous devices that data processing service 134 may use on the stored or parameterized data.

In some embodiments, data processing service 134 may reduce bandwidth requirements between server 110 and the heterogeneous devices by aggregating data centrally so that only the aggregated data is distributed among the heterogeneous devices. In some embodiments, data processing service 134 may additionally streamline the aggregation of data from many different heterogeneous devices.

Logging service 135 provides the ability to log data and/or events provided by the heterogeneous devices. Using one or more logs, logging service 135 may be configured to record data and events along with timestamps. For example, a log may be configured to record updates made to specific data items stored using blackboard service 132 and/or to record updates made by specific heterogeneous devices. In some embodiments, logging service 135 may also support a user interface (not shown) for configuring logging service 135, accessing recorded logs, and/or managing recorded logs. In some examples, the user interface may access logging service 135 remotely from a separate computer or workstation. In some embodiments, logging service 135 may also support time synchronization between server 110 and the heterogeneous devices to ensure that timestamps being recorded across the one or more logs consistently reflect the actual time of data updates and events. In some examples, logging service 135 may exchange one or more synchronization messages with the heterogeneous devices to more accurately model effects associated with latency associated with processing and/or communication delays between server 110 and the heterogeneous devices, clock skew, and/or clock surgical table. In some examples, logging service 135 may use compression, such as that provided by compression service 141 to reduce the size of the recorded logs.

In some embodiments, logging service 135 may record the logs in memory and/or some type of persistent storage device. In some examples, the logs may be recorded using a disk drive or similar storage medium located in server 110. In some examples, the logs may be recorded using a disk drive or storage medium located in a separate workstation (not shown).

In some embodiments, logging service 135 may also make the one or more logs available for offline use. In some examples, the one or more logs may be used to evaluate, test, and/or debug individual heterogeneous devices and/or to coordinate among the heterogeneous devices. In some examples, the one or more logs may be data mined and/or subject to analysis to evaluate, for example, the efficiency of a heterogeneous device. In some examples, the one or more logs may be used to synthesize one or more models and/or atlases based on the logged information, such as representative and/or test trajectories of movable devices. In some examples, the one or more logs may be made available to replay service 138.

Alert service 136 provides the ability to send synchronous and/or asynchronous notifications to the heterogeneous devices. Unlike publisher service 133, alert service 136 is not necessarily restricted for use with data updates. In some embodiments, alert service 136 may be used to share asynchronous notifications associated with interrupts, exceptions, emergency stop events, and/or other events between the heterogeneous devices. For example, an oxygen sensor may use alert service 136 to notify other heterogeneous devices, such as a cautery tool, that an unsafe level of oxygen is detected. In some embodiments, alert server 136 may be used to share synchronous notifications, such as those associated with a time keeping system that issues periodic time synchronization messages and/or heartbeat messages.

Token service 137 provides a system for sharing coordination tokens among the heterogeneous devices. Using token service 137, heterogeneous devices may request and release coordination tokens. As needed, heterogeneous devices may be blocked from further action when they cannot obtain the desired coordination tokens. Coordination tokens may include mutually exclusive (MUTEX) tokens, multiple use tokens, and/or special-purpose tokens as needed by the heterogeneous devices. In some examples, a MUTEX token may be used to avoid race and/or deadlock conditions between two heterogeneous devices, such as may occur when two movable devices are using collision avoidance strategies and only one movable device at a time should be moving. In some examples, multiple use tokens may be issued to a limited number of heterogeneous devices so that a shared resource is made available only to the number of heterogeneous devices that the shared resource may support. In some embodiments, special-purpose tokens may be used to coordinate specific activities among the heterogeneous devices.

In the context of coordinated movement, the special-purpose tokens may include exclusive-motion tokens, follow-me tokens, collision-avoidance tokens, and/or the like. An exclusive-motion token may be used when only a single movable device is permitted to move. In some examples, a movable device may be any device capable of autonomous and/or semi-autonomous movement of one or more elements coupled to the device. In some examples, a movable device may include a device where either part or all of the device may be moved. Only the movable device holding the exclusive-motion token may be allowed to move. In some examples, the movable device holding the exclusive-motion token may use positioning data from other devices that is stored using blackboard service 132 to plan a motion path that is collision free. A follow-me token may be used when one of two or more movable devices is executing a movement that the other movable device or devices should follow. In some examples, the movable device or devices holding a follow-me token may use motion path planning and/or other positioning data that is stored using blackboard service 132 to plan a compliant trajectory. A collision-avoidance token may be used when a primary movable device needs to execute a motion and one or more other secondary movable devices should move out of the way of the primary movable device as it moves. In some examples, the follow-me token and the collision-avoidance token may involve multiple sub-tokens, an exclusive master token held by the primary movable device, and other sharable slave tokens held by the secondary movable devices. In some examples, the secondary movable device or devices may use path planning and/or other positioning data from the primary movable device that is stored using blackboard service 132 to plan a compliant and/or collision-free trajectory. In some embodiments, token service 137 may be used by one movable device to assign a specific movement token to another movable device. In some examples, the assignment of movement tokens may be used by a movable device holding a master token to assign one or more slave tokens to corresponding one or more other movable devices as necessary. In some examples, a movable device planning to perform a motion may assign a passive collision-avoidance token on one or more other movable devices. The passive collision-avoidance token or tokens may be used to restrict and/or prohibit motion in the other movable device or devices as well as request that the other movable device or devices periodically report their current position. In some examples, the movable device requesting assignment of a movement token may wait for confirmation of the assignment before performing any motion. In some examples, token service 137 may also use alert service 136 to coordinate the issuance and/or assignment of the various sub-tokens.

Replay service 138 provides a system for replaying data streams and/or events from one or more logs. In some embodiments, replay service 138 may be used to review and/or recreate a surgery or other procedure in a simulated environment for training and/or evaluation purposes. In some embodiments, replay service 138 may be used in a system to emulate one or more of the heterogeneous devices as playback devices. In some examples, a computer-assisted surgical device may be used in an environment with a simulated imaging device for the purposes of procedure planning and the like. The logged series of images from the imaging device may be replayed by replay service 138 using the recorded timestamps for sequencing while the computer-assisted surgical device is operated live. In some examples, the playback imaging device may be used with replayed trajectory data of the computer-assisted surgical device to plan the best trajectory a movable medical imaging device can take for capturing a desired image of a patient while avoiding collision with the computer-assisted surgical device. In some examples, replay service 138 may be used with previously logged trajectory data to test and/or evaluate follow-me or collision-avoidance algorithms without the risk of actual collisions between movable devices and/or danger to an actual patient. In some embodiments, replay service 138 may also replay synthetic data based on models from logged data and/or simulations from vendors. In some embodiments, replay service 138 may be used in conjunction with a mix of live, recorded, simulated, and/or synthetic heterogeneous devices.

Encryption service 139 provides a system for decoupling encryption and decryption processes and/or algorithms from the other services coupled to shared interface 120. By decoupling encryption and decryption from the other services, users of shared interface 120 may install and/or operate different encryption and decryption processes and algorithms without having to embed that functionality into one of the other services. Encryption service 139 may provide any kind of encryption and decryption such as symmetric key encryption, public-key encryption, private-key encryption, and/or the like. Encryption services 139 may further provide data integrity services such as check summing, CRC coding, MD5, and/or other such services.

Compression service 140 provides a system for decoupling compression and decompression processes and/or algorithms from the other services. By decoupling compression and decompression from the other services, users of shared interface 120 may install and/or operate different compression and decompression processes and algorithms without having to embed that functionality into one of the other services. Compression services 140 may provide any kind of compression and decompression including lossless compression and decompression such as Lempel-Ziv-Welch (LZW) compression, and/or the like and/or lossy compression such as JPEG, MPEG, and/or the like.

Vendor services 141 provides a system for allowing the heterogeneous devices to make additional services available among themselves. In some embodiments, vendor services 141 may provide registration for sharing the existence of available services in the heterogeneous devices. In some examples, vendor services 141 may include a registry or catalog of available services including interface specifications so that other heterogeneous devices may use the available services. In some examples, the interface specifications may include definitions similar to those used to publish and share web services. In some examples, vendor services 141 may provide locating and/or forwarding services that may couple heterogeneous devices wanting to use an available service to the heterogeneous device hosting the service.

Emergency stop service 142 provides support for safe shutdown and/or support for other graceful failure operations among the heterogeneous devices using server 110 and/or shared interface 120. In some examples, emergency stop service 142 may work in cooperation with alert service 136 to either monitor activity among the other services and/or the heterogeneous devices or to provide emergency stop and/or other failure alerts to the other services and/or the heterogeneous devices. For example, emergency stop service 142 may be used to transmit a stop moving alert to each of the heterogeneous devices that are capable of movement. Although not shown in FIG. 1, in some examples, emergency stop service 142 may be coupled to one or more dead-man switches, watchdog timers, watchdog relays, and/or other emergency stop and watchdog devices. In some examples, emergency stop service 142 may be further coupled to one or more shared safety circuits (not shown) with dedicated wiring to each of the heterogeneous devices to share emergency stop signals with each of the heterogeneous devices. In some examples, the shared safety circuits may include both primary and backup secondary circuits.

Server 110 further includes a plurality of hardware ports 150 for coupling server 110 to the heterogeneous devices. In some examples, one or more of the hardware ports 150 may provide support for standardized hardware interfaces such as universal serial bus (USB), firewire (IEEE 1394), RS232, RS485, CAN, Fieldbus, Profibus, inter-integrated circuit (I2C), and/or the like. In some examples, one or more of the hardware ports 150 may provide support for coupling server 110 to local area networks (LANs) such as Ethernet and/or wide-area networks (WANs) such as an internet. In some examples, one or more of the hardware ports 150 may be provided through custom-designed and/or vendor-specific interface cards that may be installed in server 110 using slots that support standards such as peripheral component interconnect express (PCIe), ExpressCard, and/or the like.

As shown in FIG. 1, interoperability system 100 further includes a link 155 coupling one of the hardware ports 150 of server 110 to an exemplary heterogeneous device as depicted by a node 160 at a port 165. In some embodiments, data transferred using link 155 may be encrypted. Like server 110, node 160 may include one or more processors and memory. Additionally, port 165 may be similar to any of the ports 150. In some embodiments, node 160 may be any of many types of heterogeneous devices including an imaging device, a picture archiving and communication system (PACS) station, a computer-assisted surgical or interventional device, a focal therapy device, a localization device, a positioning device, a tracking device, a monitoring device, a surgical table, a smart floor or wall supporting navigation, display, and/or other technologies, a camera, a range sensor, an environment sensor, a tracking device, and/or the like. The imaging device may be an ultrasound, x-ray, CT, MRI device, a gamma probe, and/or the like. The monitoring device may include a cardiac monitor, a respiration monitor, and/or the like. The range sensor may include a SONAR device, a LIDAR device, and/or the like. The environment sensor may include a heat sensor, a pressure sensor, a humidity sensor, an oxygen sensor, and/or the like. In some examples, the tracking device may include one or more tracking technologies based on vision, electromagnetics, RFID, ultrasonics, articulated mechanical systems, and/or the like.

Like server 110, node 160 includes a shared interface 170. For example, shared interface 170 may be using APIs and/or software development kits (SDKs) that permit node 160 to take advantage of shared interface 120 and the services 131-142 of server 110. In some examples, shared interface 170 may be a local version of shared interface 120.

Node 160 further includes one or more applications 172 that use shared interface 170 to access shared interface 120 and services 131-142. The applications 172 permit node 160 to be an active participant in interoperability system 100. The one or more applications 172 may, for example, register with server 110 using registration service 131, use blackboard service 132 to exchange data and information with other heterogeneous devices and nodes, enable logging using logging service 135 and/or the like. In other examples, when node 160 is a movable device, the applications 172 may include motion planning and execution algorithms that use the specialized tokens from token service 137 and data from blackboard service 132 to coordinate motion with one or more other movable devices.

Node 160 may further include one or more services 174 that also use shared interface 170. In some embodiments, the services 174 may include services that asynchronously or synchronously share data and information from node 160 to blackboard service 132 to be shared with other heterogeneous devices and/or node. In some examples, the services 174 may include a service that sends new images taken by an imaging device to blackboard service 132 for sharing. In some examples, the services 174 may include a service that synchronously updates the location coordinates of a movable device.

In some embodiments, the services 174 may include shared services that node 160 may make available to other heterogeneous devices and/or nodes in interoperability system 100 using, for example, vendor services 141. In some examples, the shared services may include any of the services 131-142 and/or additional services being provided by node 160. In some examples, the shared services of node 160 may include access to parameterized processing scripts that preprocess data before it is sent for sharing to blackboard service 132. As an example, a parameterized processing script in an imaging device may accept parameters for a proprietary imaging processing algorithm that may be applied to images before they are shared. Using this parameterized processing script, other heterogeneous devices and/or nodes may request customized versions of images.

Node 160 may also include support for a user interface 176. User interface 176 may be used to manage and/or control applications 172 and/or services 174. In some examples, user interface 176 may be used to control which services 174 are available to other heterogeneous devices and/or nodes in system 100. In some examples, user interface 176 may be used to control the rate at which data is sent to blackboard service 132. In some examples, user interface 176 may be used to control which data and/or events are to be logged by logging service 135. In some embodiments, user interface 176 may be a graphical user interface. In some embodiments, user interface 176 may be accessed using a control panel and/or monitor screen, such as a touch screen, on node 160. In some embodiments, user interface 176 may be remotely accessed using a terminal, a workstation, a surgical console, and/or the like coupled to node 160 over a network.

As further shown in FIG. 1, interoperability system 100 may further include any number of nodes and/or heterogeneous devices. Two such additional nodes are shown as nodes 181 and 189, which represent a range of nodes from node 181 to node 189. Like node 160, node 181 includes a version of the shared interface as well as applications, services, and/or a user interface. Node 181 is coupled to server 110 using link 191. Similarly, node 189 includes a version of the shared interface as well as applications, services, and/or a user interface and is coupled to server 110 using link 199. Each of nodes 181-189 represents a heterogeneous device and may be different from or the same model as any of the other nodes 160 and 181-189, such that it is possible that nodes 160 and 181-189 may include two or more medical devices that are the same.

Figure 2:
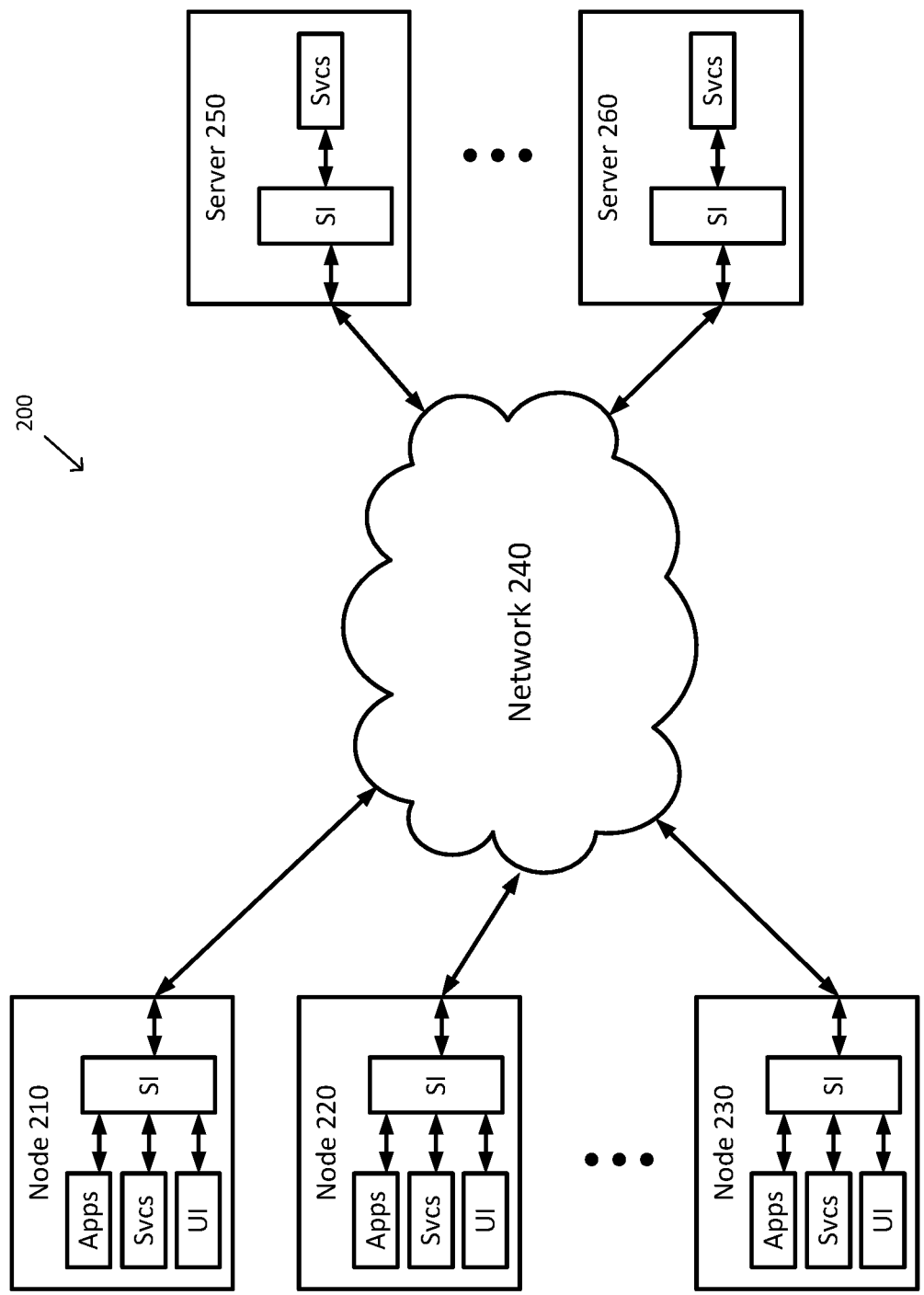
FIG. 2 is a simplified diagram of another interoperability system according to some embodiments.

FIG. 2 is a simplified diagram of another interoperability system 200 according to some embodiments. As shown in FIG. 2, interoperability system 200 includes several heterogeneous medical devices or nodes 210-230. Although three nodes are depicted in interoperability system 200, interoperability system 200 may include any number of nodes. Nodes 210-230 are similar to nodes 160 and 181-189. Each of the nodes 210-230 may include a version of the shared interface, applications, services, and/or a user interface as described above.

Each of the nodes 210-230 is coupled using a network 240 to servers 250 and 260. Network 240 may be any kind of network, including a LAN and/or a WAN. Servers 250 and 260 may be similar to server 110 and may each include a version of shared interface 120 and/or services 131-142. Although two servers are depicted in interoperability system 200, interoperability system 200 may include any number of servers, including no servers when the shared interface 120 is distributed across nodes 210-230. Depiction of servers 250 and 260 underscores the flexible nature of the shared interfaces 120 and 170 and interoperability system 200 as the services 131-142 and 172 may potentially be hosted in any combination on the nodes 210-230 and servers 250 and 260. In some embodiments, servers 250 and 260 may be omitted and the services 131-142 may be hosted entirely on node 210 or on any combination of the nodes 210-230. In some embodiments, any of the nodes 210-230 may be combined into the same workstation or cluster as any of the servers 250-260. In some embodiments, server 260 may be a mirror of server 250 providing backup and/or fail over support for server 250. In some embodiments, services 131-142 may be duplicated among servers 250 and 260. In some examples, server 250 may include a version of logging services 135 that is used for logging certain types of data, and server 260 may include another version of logging services 135 that is used for logging other types of data. In some embodiments, interoperability system may include only a limited server or hub that may provide only registration service 131 and vendor services 141, with vendor services 141 being used to locate and direct service requests to the nodes 210-230 hosting the other services 132-140 and/or 142.

Figure 3:
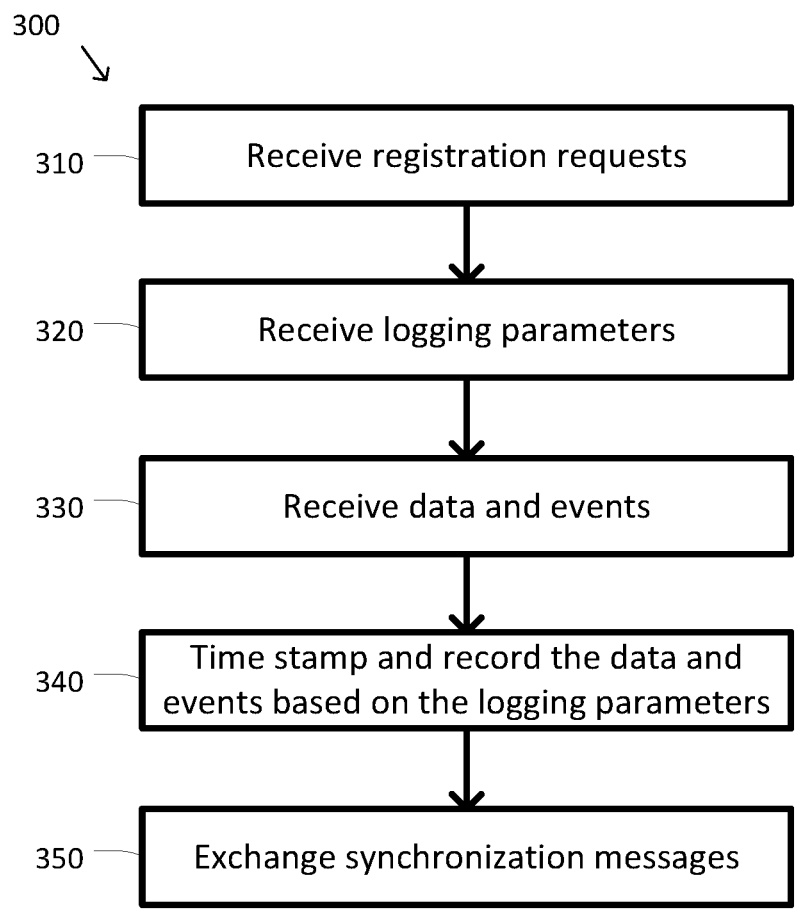
FIG. 3 is a simplified diagram of a method of logging information according to some embodiments.

FIG. 3 is a simplified diagram of a method 300 of logging information according to some embodiments. One or more of the processes 310-350 of method 300 may be implemented, at least in part, in the form of executable code stored on non-transient, tangible, machine readable media that when run by one or more processors (e.g., one or more processors in nodes 160, 181-189, and/or 210-230 and/or in the servers 110, 250, and/or 260) may cause the one or more processors to perform one or more of the processes 310-350. In some embodiments, one or more of the processes 310 and/or 350 are optional and may be omitted. In some embodiments, the method 300 may be performed by a service, such as logging service 135.

At an optional process 310, registration requests are received. In order to use logging services, such as logging service 135, one or more nodes, such as nodes 160, 181-189, and/or 210-230, may register themselves with a shared interface, such as shared interface 120. For example, the one or more nodes may make a registration request that is received by registration service 131. In some examples, registration service 131 may respond by supplying each of the one or more nodes with a respective key and/or a session identifier used to identify the respective node with the shared interface and/or logging service 135.

At a process 320, one or more logging parameters are received. For example, the one or more nodes may use the shared interface to specify which data and/or events supplied by the respective node should be recorded and in which log or logs the data and/or events should be recorded. For data which is provided by the one or more nodes using blackboard service 132, the data to log may be identified by the respective key identifying the data. In some embodiments, the one or more logging parameters may further include one or more interval specifications for controlling how often data should be logged. In some examples, the one or more interval specifications may specify a fixed, but configurable interval, at which the data is to be logged. In some examples, the one or more interval specifications may specify that data should only be logged whenever it is updated.

At a process 330, data and events are received. As the one or more nodes supply data and/or trigger one or more events, they are received by the shared interface. In some examples, data may be received from the one or more nodes via blackboard service 132 and forwarded to logging service 135. In some examples, the data may be processed by data processing services 134, encryption service 139, and/or compression service 140 before being forwarded to logging service 135. In some examples, one or more events may be generated through publisher service 133 and/or alert service 136.

At a process 340, the data and events are time stamped and recorded based on the logging parameters. Based on the one or more logging parameters received during process 320, the data and/or one or more events received during process 330 are recorded in one or more logs. To facilitate playback and/or review later, each entry in the log may be associated with a timestamp. In some examples, the timestamp may reflect a time at which the data was received by the logging service 135 and/or a time associated with the node that transmitted the data to logging service 135. In some examples, the timestamp may indicate when an event occurred. In some embodiments, the timestamps may be adjusted by the logging service 135 due to clock surgical table between the one or more nodes and the server or node hosting the logging service 135 and/or to account for latency in communication from the one or more nodes to the logging service 135 and/or other processing delays.

At an optional process 350, synchronization messages are exchanged. In order to account for clock surgical table and/or latency in communication and processing, logging service 135 may exchange one or more synchronization messages with the one or more nodes using logging service 135. In some examples, logging service 135 may periodically send a ping-style message to each of the one or more nodes and estimate latency based on the round-trip delay in receiving a respective response message. In some examples, logging service 135 may receive one or more current time messages from each of the one or more nodes and use any latency estimates to estimate clock surgical table between the current time in the logging service 135 and the respective node. In some examples, logging service 135 may exchange one or more time synchronization messages with one or more nodes and/or one or more servers also running a logging service to synchronize clock references between logging service 135 and the one or more nodes and/or one or more servers. This supports clock synchronization among the logging services. In some embodiments, the synchronization messages may be exchanged independently of logging service 135. In some examples, a service, such as a timing service, may exchange the synchronization messages with timing services in one or more other nodes. In some examples, the timing service may share one or more latency estimates and/or one or more clock surgical table estimates with logging service 135. In some examples, the node hosting logging service 135 may exchange the one or more time synchronization messages with one or more other nodes and/or share one or more latency estimates and/or one or more clock surgical table estimates with logging service 135.

Figure 4:
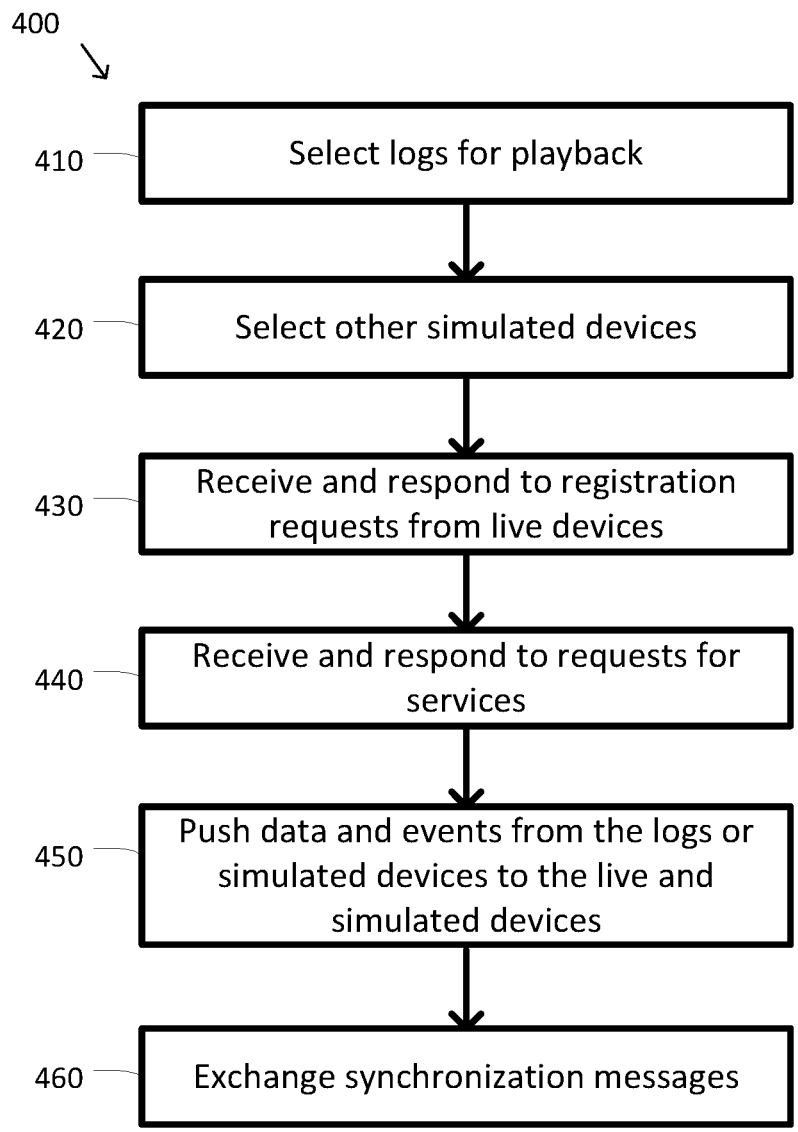
FIG. 4 is a simplified diagram of a method of replaying information according to some embodiments.

FIG. 4 is a simplified diagram of a method 400 of replaying information according to some embodiments. One or more of the processes 410-460 of method 400 may be implemented, at least in part, in the form of executable code stored on non-transient, tangible, machine readable media that when run by one or more processors (e.g., one or more processors in nodes 160, 181-189, and/or 210-230 and/or in the servers 110, 250, and/or 260) may cause the one or more processors to perform one or more of the processes 410-460. In some embodiments, one or more of the processes 420-440 and 460 are optional and may be omitted. In some embodiments, the method 400 may be performed by a service, such as replay service 138.

At a process 410, logs are selected for playback. Before a replay service, such as replay service 138 of shared interface 120 may play back information, one or more logs with the desired information are selected. Each of the one or more logs may include a sequence of one or more time-stamped entries reflecting the one or more values of data and/or one or more events that are to be played back. Once a log is selected for playback, it may become associated with a playback device and characterizes the behavior of the playback device. The user interface of replay service 138 may be used to browse and select the one or more logs for playback. In some examples, the user interface may be accessed from a remote workstation. In some examples, one or more of the logs may be stored on a server or a node hosting the shared interface. In some examples, one or more of the logs may be stored remotely from the server or node hosting the shared interface.

At an optional process 420, other simulated devices are selected. To allow for the possibility of simulated, emulated, and/or synthetic devices with replay service 138, one or more simulated devices may be selected. Each simulated device may represent a virtual device that may generate data and/or one or more events for use with the shared interface. In some examples, one or more of the simulated devices may be implemented using a custom service to be plugged into the shared interface. In some examples, one or more of the simulated devices may be implemented using a user service and/or an application hosted on one of the nodes in the logging and playback system. In some examples, the user service may be hosted on the same node as a live device. In some examples, the user service may provide a simulated device in place of the live device. In some examples, the user interface of replay service 138 may be used to browse and/or select from a catalog of simulated devices that are available for playback. In some examples, the user interface may be accessed from a remote workstation.

At an optional process 430, registration requests are received. In order to use replay services, such as replay service 138, one or more nodes such as nodes 160, 181-189, and/or 210-230 may register themselves with a shared interface, such as shared interface 120. By registering themselves with the shared interface, the one or more nodes may indicate that they are live devices that will be present and using the shared interface during the playback process. In some embodiments, registration requests may also be received from the one or more simulated devices selected during process 420. For example, the one or more nodes and/or the one or more simulated devices may make a registration request that is received by registration service 131. In some examples, registration service 131 may respond by supplying each of the one or more nodes with a respective key and/or a session identifier used to identify the respective node with the shared interface and/or replay service 138.

At an optional process 440, requests for service are received and responded to. In essentially the same way the shared interface receives and responds to service requests when replay service 138 is not in use, the services 131-137 and/or 139-142 may receive one or more requests from the one or more live devices and/or one or more simulated devices and respond appropriately. In effect, even though replay is being performed, shared interface 120 operates in its normal fashion.

At a process 450, data and events from the logs and/or simulated devices is pushed to the live and/or simulated devices. Replay service 138 may extract data and/or one or more events from one or more entries in the one or more logs and recreate the one or more service requests that generated them. For example, a data update recorded in one of the one or more logs may result in recreation of a corresponding service request to be initiated and/or sent to blackboard service 132. In some examples, this may in turn trigger publishing by publication service 133, one or more alerts by alerting service 136, and/or the like. In some examples, one or more requests for and/or one or more grants of tokens using token service 137 may also be replayed by replay service 138. Where appropriate the one or more responses to the one or more log entries, such as a publication by publisher service 133, may be pushed to the one or more live devices and/or the one or more simulated devices. In some examples, one or more responses directed to a playback device emulated by a log may be ignored. In some examples, one or more responses directed to a playback device emulated by a log may be compared with one or more other log entries in the log to confirm behavior consistent with that found in the log and/or to flag an error when appropriate. In some embodiments, the timestamp associated with each log entry may be used to sequence and/or control the timing of the playback of the log entry. In some examples, the playback may be adjusted to account for latency and/or other delays during playback.

According to some embodiments, the data and/or one or more events pushed to the one or more live devices and/or one or more simulated devices may be generated by fusion between one or more logs and one or more simulated devices. In some examples, one or more entries from one or more logs may be directed to a console associated with one or more simulated devices. In some examples, the console may control the behavior of the one or more simulated devices based on the one or more entries. In some examples, the console may be suitable for training purposes where the one or more logs recreate a procedure that an operator and/or a trainee at the console may mirror and/or recreate. In some examples, one or more inputs from the trainee using the console may be used to adjust behavior of the one or more simulated devices. In some examples, the one or more inputs may be associated with manipulation of controls by the trainee. In some examples, the adjusted behavior may alter the pushing of the data and/or one or more events associated with the one or more log entries or the one or more simulated devices. In some examples, the adjusted behavior may include altering timing of the pushing of the data and/or one or more events. In some examples, the fusion may involve more than one console and/or more than one operator or trainee.

At an optional process 460, synchronization messages are exchanged. In order to account for clock surgical table and/or latency in communication and processing, replay service 138 may exchange one or more synchronization messages with the one or more live devices and/or one or more simulated devices using replay service 138. In some examples, replay service 138 may periodically send a ping-style message to each of the one or more live devices and/or one or more simulated devices and estimate latency based on the round-trip delay in receiving a respective response message. In some examples, replay service 138 may receive one or more current time messages from each of the one or more live devices and/or one or more simulated devices and use any latency estimates to estimate clock surgical table between the current time in the replay service 138 and the live device or simulated device. In some examples, replay service 138 may exchange one or more time synchronization messages with one or more nodes and/or one or more servers also running a replay service to synchronize clock references between replay service 138 and the one or more nodes and/or one or more servers. This supports clock synchronization among the replay services. In some embodiments, the synchronization messages may be exchanged independently of replay service 138. In some examples, a service, such as a timing service, may exchange the synchronization messages with timing services in one or more other nodes. In some examples, the timing service may share one or more latency estimates and/or one or more clock surgical table estimates with replay service 138. In some examples, the node hosting replay service 138 may exchange the one or more time synchronization messages with one or more other nodes and/or share one or more latency estimates and/or one or more clock surgical table estimates with replay service 138.

In some embodiments, method 400 may be used with a recreation system running on a workstation. The one or more played back events, logging events, and/or any service responses may be forwarded to the recreation system. In some examples, the recreation system may be used to demonstrate the behavior of the live, simulated, and/or playback devices in a virtual environment. In some examples, the recreation system may include one or more virtual models for each of the live, simulated, and/or playback devices that allow the recreation engine to recreate all of the data and/or events known to the shared interface 120 and the replay service 138. In some examples, when only playback devices are present, the recreation engine may provide a virtual reconstruction of all of the logged entries.

In some embodiments, the workstation running the recreation system may also host a shared interface and one or more services, including a replay service 138. During process 410, one or more logs may be selected from the workstation and/or one or more servers hosting one or more repositories of one or more logs. The selected one or more logs may be used to create a virtual reconstruction using only corresponding one or more playback devices. In some examples, the one or more logs in one of the repositories may be aggregated into one or more atlases. Each of the atlases may include one or more composite logs formed by creating a composition of one or more other logs. In some examples, a composite log may be formed by aggregating related entries in each of the one or more other logs. In some examples, related entries may be aggregated by computing an average of the same data item included in more than one of the logs. In some examples, related entries may be associated with a timestamp that is an aggregate of the timestamps for each of the related entries. In some examples, related entries may be aggregated by selecting one of the related entries. In some examples, the composite log may include each of the one or more entries included in each of the one or more other logs.

Figure 5:
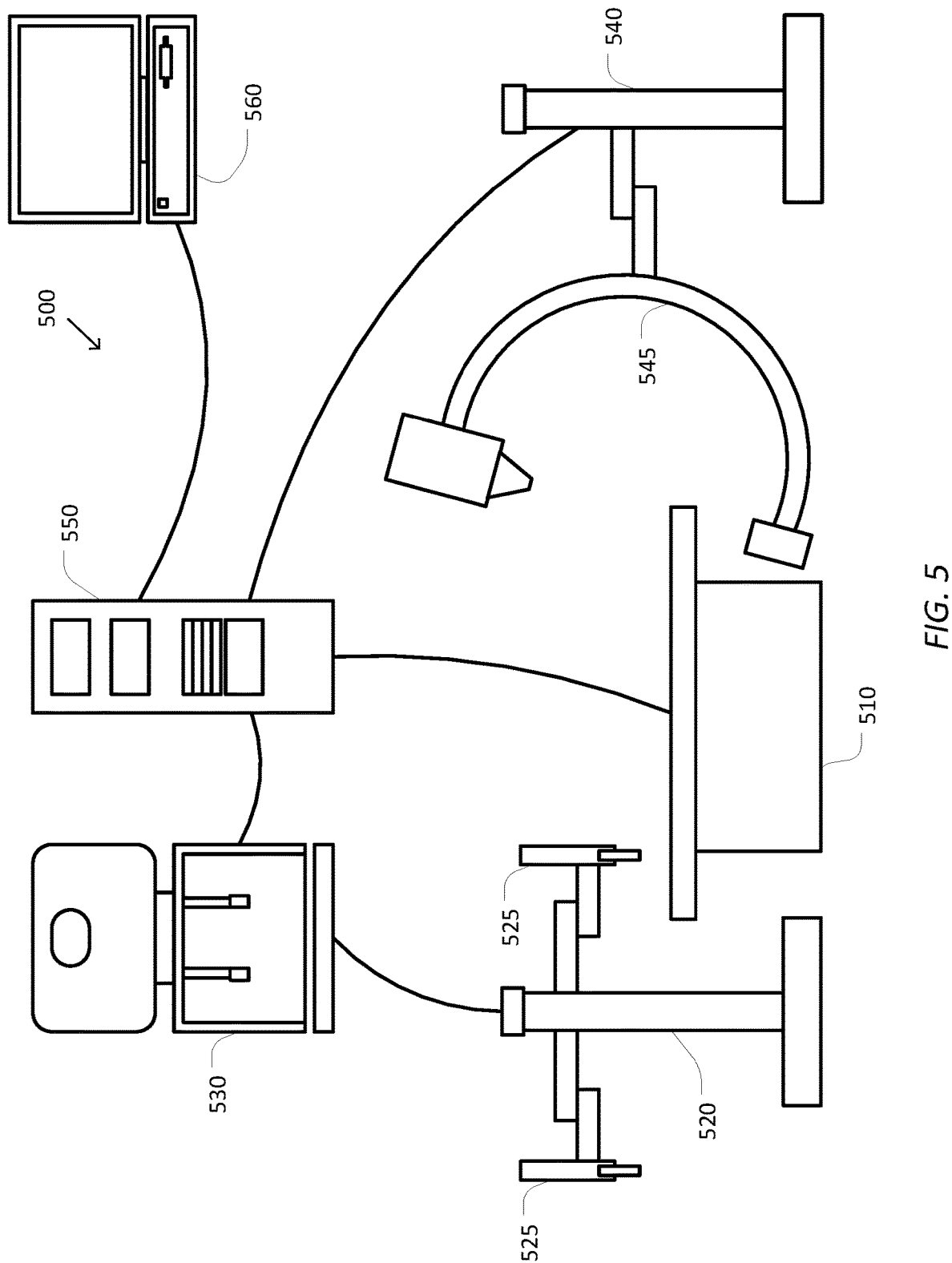
FIG. 5 is a simplified diagram of a log and replay system according to some embodiments.

FIG. 5 is a simplified diagram of a log and replay system 500 according to some embodiments. As shown in FIG. 5, log and replay system 500 may be associated with an operating room, an interventional suite and/or a partially or fully simulated environment. Log and replay system 500 includes a patient cart and/or surgical table 510. Surgical table 510 may be a movable device. In some examples, surgical table 510 may perform movement in any one of its degrees of freedom. In some examples, surgical table 510 may be adjustable in height to account for the height of doctors and/or nurses performing a procedure on a patient and/or to account for the height and/or size of one or more other devices in the vicinity of the surgical table 510. In some examples, surgical table may move laterally and/or adjust roll, pitch, and/or yaw as needed to place the patient in a suitable posture to support the current surgery and/or procedure.

Log and replay system 500 also includes a computer-assisted surgical device 520. Computer-assisted surgical device 520 may include one or more movable elements or articulated arms 525 for supporting surgical instruments, imaging devices, and/or the like. Computer-assisted surgical device 520 is further coupled to surgeon console 530, which may include one or more master controls for operating the computer-assisted surgical device 520 and/or the one or more articulated arms 525. In some embodiments, computer-assisted surgical device 520 and surgeon console 530 may correspond to a da Vinci® Surgical System commercialized by Intuitive Surgical, Inc. of Sunnyvale, California. In some embodiments, computer-assisted surgical devices with other configurations, fewer or more articulated arms, and/or the like may be used with log and replay system 500. In some embodiments, computer-assisted surgical device 520 may be mounted to surgical table 510 rather than being free-standing as depicted in FIG. 5.

Log and replay system 500 may further include an imaging device 540. Imaging device 540 includes an imaging subsystem 545 that may be used to take one or more diagnostic images of a patient located on surgical table 510.

Imaging device 540 and imaging subsystem 545 may include one or more movable elements necessary to position the imaging subsystem 545 about the patient to take the desired one or more diagnostic images. Although imaging device 540 in FIG. 5 is depicted with imaging subsystem 545 characterized as a C-arm, other types of imaging device 540 are possible in log and replay system 500. In some embodiments, imaging subsystem 545 may include a donut-shaped bore such as an MR-bore, an articulated arm with a probe, one or more articulated arms, and/or the like. In some embodiments, imaging device 540 may be mounted to surgical table 510 rather than being free-standing as depicted in FIG. 5.

The surgical table 510, the computer-assisted surgical device 520, the surgeon console 530, and/or the imaging device 540 may each be heterogeneous devices that include features similar to those found in nodes 160, 181-189, and/or 210-230. Each of these heterogeneous devices is coupled to server 550. For example, server 550 may be any of the servers 110, 250, and/or 260. Using the shared interfaces 120 and 170 as well as the services 131-142, the log and replay system 500 may implement logging and replay services consistent with the processes of methods 300 and/or 400. In some examples, the logging service may be logging service 135 and the replay service may be replay service 138.

Log and replay system 500 may further include a workstation 560. Workstation 560 may be used to access the user interface of logging service 135 and/or replay service 138. In some examples, workstation 560 may include a recreation engine that can be used to display a simulation of replayed and/or live data and events generated through replay system 138 and/or shared interface 120. In some embodiments, the recreation engine may be located in surgeon console 530 and/or server 550.

Several exemplary uses of the processes of methods 300 and/or 400 are now presented to demonstrate how logging and playback may be utilized in a system with one or more shared interfaces and associated services.

Example 1—Use for training and testing: Computer-assisted surgical device 520 and imaging device 540 may be very complex and require extensive training and testing. Doing so with a live patient may not always be practical or even prudent. Logging and replay system 500 may provide a safe and/or convenient way to provide training and/or testing of computer-assisted surgical device 520 and/or imaging device 540 using actual data from one or more real procedures. For example, one or more surgeries and/or procedures may be recorded using the logging processes of method 300. The respective logs from each of these one or more surgeries and/or procedures may allow any of surgical table 510, computer-assisted surgical device 520, and/or imaging device 540 to be replaced by corresponding virtual playback devices. In one case, one or more respective logs for each of surgical table 510 and imaging device 540 may be used to provide a simulated environment that a surgeon could use while training with a live computer-assisted surgical device 520. As the surgeon operates computer-assisted surgical device 520, replay service 138 may play back the respective one or more logs for surgical table 510 and imaging device 540 recreating conditions from an actual procedure. Similarly, one or more algorithms for computer-assisted surgical device 520 may be tested in the virtual playback environment. For example, a collision avoidance algorithm could be tested against one or more recreated motions of surgical table 510 and imaging device 540. In another case, imaging device 540 could be live with surgical table 510 and computer-assisted surgical device 520 simulated as playback devices. This would allow training and/or testing without concerns for collisions and/or patient safety as no patient or other devices need be present during the training.

In some embodiments, the training may further include fusion of data and/or one or more events from one or more logs and one or more simulated devices. In some examples, one or more entries from one or more logs may be directed to surgeon console 530 as it is being operated by the trainee. In some examples, the trainee may mirror and/or recreate a procedure captured in the one or more entries. In some examples, one or more inputs from the trainee using surgeon console 530 may be used to adjust behavior and/or movement of computer-assisted surgical device 520. In some examples, the one or more inputs may be associated with manipulation of controls on surgeon console 530 by the trainee. In some examples, the adjusted behavior may include altering replay timing of the data and/or one or more events based on the speed at which the trainee performs the procedure. In some examples, the training may extend to a second trainee operating imaging device 540 using a similar fusion of imaging device logs and inputs from the second trainee.

Example 2—Use with a simulator—Logging and playback system 500 may be used to test a simulated device and/or plan a procedure. By using one or more logs for one or more other devices in logging and playback system 500, a simulated device for one of the devices, e.g., computer-assisted surgical device 520, may either be tested and/or provide a procedure planning tool. In this situation, no live device is used, but the simulated device may be used with actual data and one or more events from one or more similar procedures. For example, this could be used by a simulated version of imaging device 540 to compare plan and/or test one or more motions to determine a best scanning path for taking an image of a patient without colliding with either a playback version of surgical table 510 and/or a playback version of computer-assisted surgical device 520.

Example 3—Procedure recreation—Logging and playback system 500 may be used to replay data and/or one or more events from one or more previous procedures. Using the logging of method 300, one or more recordings of one or more procedures using logging and playback system 500 may be created. The one or more logs may then be replayed to the recreation engine of workstation 560 to generate a virtual recreation of the movement and other data associated with the recorded procedure, including the patient data recorded in the one or more logs. This could be valuable tool for review of the procedure, morbidity and mortality reviews, and/or forensic analysis associated with a legal proceeding.

Some examples of heterogeneous devices, such as the heterogeneous devices of FIG. 5, server 550, workstation 560, and/or log and replay system 500 may include non-transient, tangible, machine readable media that include executable code that when run by one or more processors may cause the one or more processors to perform the processes of methods 300 and/or 400. Some common forms of machine readable media that may include the processes of methods 300 and/or 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method of creating a virtual recreation of a device, the method comprising:
   accessing, by a server, a log associated with a first device, wherein the server and the first device are associated with one or more surgical systems;
   extracting, by the server, a first log entry from the log;
   generating, by the server, a recreation of a first service request based on information associated with the first log entry;
   sending, by the server, the recreation of the first service request to a first shared service of a plurality of shared services to recreate an event associated with the first log entry;
   receiving, by the server from the first shared service, a response to the recreation of the first service request;
   receiving, by the server from a second device coupled to the server and associated with the one or more surgical systems, a second service request;
   responding, by the server, to the second service request;
   exchanging, by the server, one or more synchronization messages with the second device; and
   creating, by the server and based at least in part on the one or more synchronization messages, a virtual recreation of the first device based on the recreation of the first service request, the response to the recreation of the first service request, the second service request, and a response to the second service request.

2. The method of claim 1, wherein creating the virtual recreation of the first device comprises one or more of:
   using one or more models of the first device;
   providing a virtual reconstruction of each log entry in the log; or
   displaying a simulation of the recreated event.

3. The method of claim 1, wherein the second device is selected from the group consisting of a live device and a simulated device.

4. The method of claim 1, further comprising:
   receiving, by the server, a logging parameter;
   creating, by the server, a second log entry based on the logging parameter and information associated with a third service request received by the plurality of shared services;
   associating, by the server, the second log entry with a timestamp; and
   recording, by the server, the second log entry in a recording log.

5. The method of claim 4, further comprising adjusting, by the server, the timestamp based on at least one characteristic selected from the group consisting of an estimated clock skew and an estimated clock latency.

6. The method of claim 1, further comprising timing and sequencing, by the server, the recreation of the first service request based on a timestamp associated with the first log entry.

7. The method of claim 1, further comprising:
   estimating, by the server based on information associated with the one or more synchronization messages, at least one characteristic selected from the group consisting of an estimated clock skew and an estimated clock latency; and
   adjusting, by the server, timing and sequencing of the recreation of the first service request based on the at least one characteristic.

8. A logging and replay device comprising:
   a replay service;
   a recreation engine;
   one or more shared services; and
   a processor configured to execute the replay service, the recreation engine, and the one or more shared services;
   wherein the replay service is configured to:
     access a log associated with a first device, wherein the first device and the processor executing the replay service are associated with one or more surgical systems,
     extract a first log entry from the log,
     generate a recreation of a first service request for the one or more shared services based on information associated with the first log entry, and
     send the recreation of the first service request to a shared service of the one or more shared services to recreate an event associated with the first log entry;
   wherein the one or more shared services are configured to receive and respond to a second service request from a second device coupled to the logging and replay device and associated with the one or more surgical systems;
   wherein the processor executing the replay service is configured to exchange one or more synchronization messages with the second device; and
   wherein the recreation engine is configured to create, based at least in part on the one or more synchronization messages, a virtual recreation of the first device based on the recreation of the first service request, a response to the recreation of the first service request, the second service request, and a response to the second service request.

9. The logging and replay device of claim 8, wherein to create the virtual recreation of the first device, the recreation engine is configured to use one or more models of the first device.

10. The logging and replay device of claim 8, wherein to create the virtual recreation of the first device, the recreation engine is configured to provide a virtual reconstruction of each log entry in the log.

11. The logging and replay device of claim 8, wherein the recreation engine is further configured to display a simulation of the recreated event.

12. The logging and replay device of claim 8, wherein the second device is selected from the group consisting of a live device and a simulated device.

13. The logging and replay device of claim 8, wherein:
   the one or more shared services includes a logging service; and
   the logging service is configured to:
     receive a logging parameter,
     create a second log entry based on the logging parameter and information associated with a third service request received by the shared services,
     associate the second log entry with a timestamp, and
     record the second log entry in a recording log.

14. The logging and replay device of claim 13, wherein the logging service is further configured to adjust the timestamp based on at least one characteristic selected from the group consisting of an estimated clock skew and an estimated clock latency.

15. The logging and replay device of claim 8, wherein the replay service is further configured to time and sequence the recreation of the first service request based on a timestamp associated with the first log entry.

16. The logging and replay device of claim 8, wherein the replay service is further configured to:
    estimate at least one characteristic based on information associated with the one or more synchronization messages, the at least one characteristic selected from the group consisting of: a clock skew and a clock latency; and
    adjust timing and sequencing of the recreation of the first service request based on the at least one characteristic.

17. A non-transitory machine-readable medium comprising a plurality of machine-readable instructions which when executed by one or more processors of a server are adapted to cause the one or more processors to perform a method comprising:
    accessing a log associated with a first device, wherein the server and the first device are associated with one or more surgical systems;
    extracting a first log entry from the log;
    generating a recreation of a first service request based on information associated with the first log entry;
    sending the recreation of the first service request to a first shared service of a plurality of shared services to recreate an event associated with the first log entry;
    receiving, from the first shared service, a response to the recreation of the first service request;
    receiving, from a second device coupled to the server and associated with the one or more surgical systems, a second service request;
    responding to the second service request;
    exchanging one or more synchronization messages with the second device; and
    creating, based at least in part on the one or more synchronization messages, a virtual recreation of the first device based on the recreation of the first service request, the response to the recreation of the first service request, the second service request, and a response to the second service request.

18. The non-transitory machine-readable medium of claim 17, wherein creating the virtual recreation of the first device comprises one or more of:
    using one or more models of the first device;
    providing a virtual reconstruction of each log entry in the log; or
    displaying a simulation of the recreated event.

19. The non-transitory machine-readable medium of claim 17, further comprising timing and sequencing the recreation of the first service request based on a timestamp associated with the first log entry.

20. The non-transitory machine-readable medium of claim 17, further comprising:
    estimating, based on information associated with the one or more synchronization messages, at least one characteristic selected from the group consisting of an estimated clock skew and an estimated clock latency; and
    adjusting timing and sequencing of the recreation of the first service request based on the at least one characteristic.

* * * * *

UNITED STATES PATENT AND TRADEMARK OFFICE
CERTIFICATE OF CORRECTION

PATENT NO. : 12,131,172 B2
APPLICATION NO. : 17/544654
DATED : October 29, 2024
INVENTOR(S) : Mahdi Azizian et al.

Page 1 of 1

It is certified that error appears in the above-identified patent and that said Letters Patent is hereby corrected as shown below:

On the Title Page

(63) Related U.S. Application Data:
Please delete "Continuation of application No. 16/142,937, filed on Sep. 26, 2018, now Pat. No. 11,221,863, which is a continuation of application No. 14/912,079, filed as application No. PCT/US2014/051055 on Aug. 14, 2014, now Pat. No. 10,127,060." and insert --Continuation of application No. 16/142,937, filed on Sep. 26, 2018, now Pat. No. 11,221,863, which is a continuation of application No. 14/912,079, filed on Feb. 12, 2016, now Pat. No. 10,127,060, which is a 371 of application No. PCT/US2014/051055, filed on Aug. 14, 2014.--.

Signed and Sealed this
Sixth Day of January, 2026

John A. Squires
*Director of the United States Patent and Trademark Office*